United States Patent [19]
Okawa et al.

[11] Patent Number: 5,814,728
[45] Date of Patent: Sep. 29, 1998

[54] NONDESTRUCTIVE INSPECTION METHOD OF POLYMER INSULATOR AND APPARATUS FOR PERFORMING THE SAME

[75] Inventors: Yasushi Okawa, Kasugai; Itsushi Nakamura, Nagoya; Tomio Suzuki, Yokkaichi; Masahiro Hori, Nagoya, all of Japan

[73] Assignee: NGK Insulators, Ltd., Japan

[21] Appl. No.: 824,954

[22] Filed: Mar. 27, 1997

[30] Foreign Application Priority Data

Mar. 28, 1996 [JP] Japan ................................. 8-073686
Nov. 8, 1996 [JP] Japan ................................. 8-296217

[51] Int. Cl.⁶ .................................................. G01N 29/14
[52] U.S. Cl. ............................. 73/587; 73/799; 73/801; 364/508
[58] Field of Search ........................... 73/801, 799, 587, 73/661, 579, 602; 364/507, 508; 174/182, 189

[56] References Cited

U.S. PATENT DOCUMENTS

| 3,924,456 | 12/1975 | Vahaviolos | 73/587 |
| 4,004,456 | 1/1977 | Vahaviolos | 73/587 |
| 4,089,224 | 5/1978 | Scott et al. | 73/587 |
| 4,107,981 | 8/1978 | Kanagawa et al. | 73/587 |
| 4,494,408 | 1/1985 | DeLacy | 73/587 |
| 4,565,964 | 1/1986 | Matthews et al. | 324/51 |
| 5,453,291 | 9/1995 | Sasahara et al. | 427/8 |

FOREIGN PATENT DOCUMENTS 60-44841  4/1981  Japan .

Primary Examiner—Hezron E. Williams
Assistant Examiner—Rose M. Miller
Attorney, Agent, or Firm—Parkhurst & Wendel

[57] ABSTRACT

A nondestructive inspection method of inspecting a securing defect of a polymer insulator having an FRP core, an outer cover portion arranged around the FRP core, and at least one metal member secured to at least one end of the FRP core, includes the steps of; measuring an acoustic emission signal generated when the metal member is secured to the FRP core by using compression dies; and determining whether or not the securing defect is generated on the basis of the acoustic emission signal in process. Moreover, the disclosed apparatus performs the nondestructive inspection method mentioned above.

7 Claims, 6 Drawing Sheets

FIG_1

FIG._2

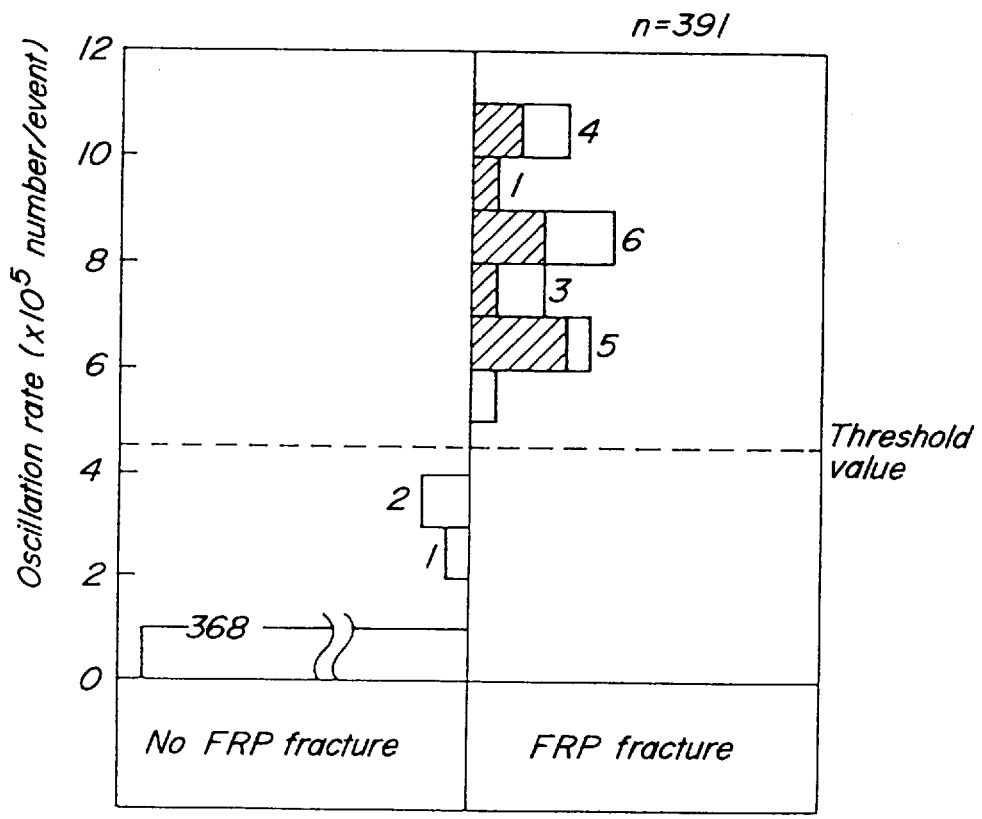

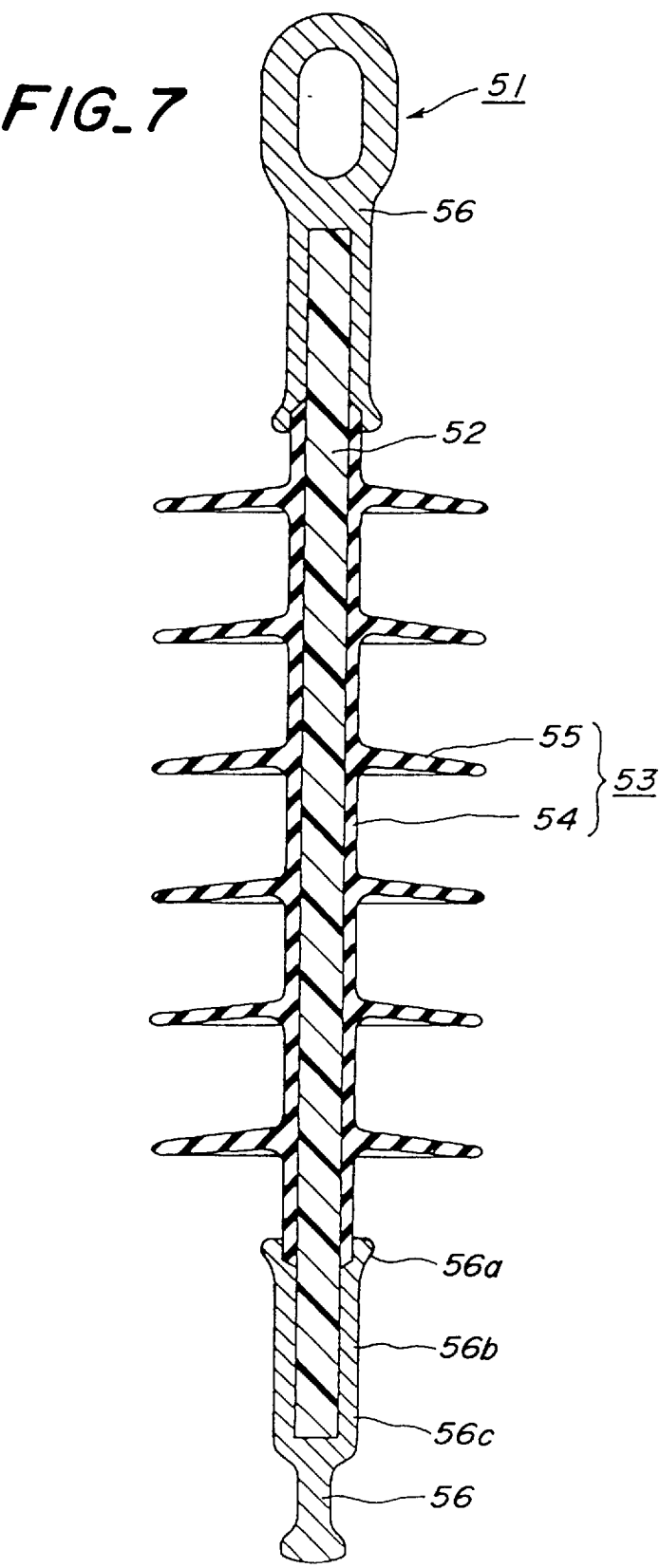
FIG_7

NONDESTRUCTIVE INSPECTION METHOD OF POLYMER INSULATOR AND APPARATUS FOR PERFORMING THE SAME

BACKGROUND OF THE INVENTION (1) Field of the Invention

The present invention relates to a nondestructive inspection method and apparatus of measuring a securing defect of a polymer insulator having an FRP core, an outer cover portion arranged around the FRP core, and at least one metal member secured to at least one end of the FRP core.

(2) Related Art Statement

A polymer insulator having an FRP core, an outer cover portion arranged around the FRP core, and at least one metal member secured to at least one end of the FRP core is generally known. FIG. 7 is a cross sectional view showing one embodiment of the polymer insulator to which the present invention can be applied. In the embodiment shown in FIG. 7, a polymer insulator 51 comprises an FRP core 52 and an outer cover portion 53. The outer cover portion 53 comprises a sheath portion 54 arranged on an overall outer surface of the FRP core 52 and a plurality of shed portions 55 projected from the sheath portion 54. Moreover, metal members 56 are secured to both end portions of the FRP core 52.

Whether or not the polymer insulator 51 mentioned above passes a tensile strength test is performed as follows on the basis of the IEC standard or the like. At first, a preliminarily tensile test for all the polymer insulators 51 is performed under such a condition that a load applied thereto is 50% of specified mechanical load. Then, a predetermined number of polymer insulators 51 which pass the preliminarily tensile test are picked up from every product lot in response to the number of products in the product lot, and are subjected to a tensile breaking load test. As a result, the product lot in which all the picked up products satisfy a reference value is deemed a successful product lot.

The examination method mentioned above is assumed to be highly reliable. However, there remains a problem such that whether or not the examination method mentioned above can perform a sufficient defect detection for a long term reliability. For example, when the metal members 56 are secured to the both end portions of the FRP core 52 even in the polymer insulator 51 which passes the examination mentioned above, it is believed that a micro crack is sometimes generated in the FRP core 52 positioned at an inner portion of the metal member 56. This is because controls of a surface roughness on an inner surface of the metal member 56 and a pressure applying method are not performed correctly. Such a micro crack can not be detected from an appearance of the polymer insulator 51 unless the polymer insulator 51 is dismembered, and thus it is necessary to perform a nondestructive measurement for the polymer insulator 51. Therefore, in order to improve the reliability of the polymer insulator and to use it safely for a long term, a defect inspection method after securing for the FRP core positioned at an inner portion of the metal member is desirable.

Moreover, in an extreme case such that a surface roughness on an inner surface of the metal member is rough and a pressure applying method is bad, the FRP core 52 itself is sometimes fractured within the metal member 56. If such a fractured position of the FRP core 52 is at an inlet portion 56a of the metal member 56, it is possible to detect and eliminate such a fractured polymer insulator substantially completely by the examination method mentioned above, since a tensile strength is decreased due to a decrease of a securing area. However, if such a fractured position is at an intermediate portion 56b or at a bottom portion 56c of the metal member 56, a tensile strength is increased as compared with the case mentioned above, since a remaining securing method is increased gradually from the intermediate portion 56b to the bottom portion 56c as compared with the inlet portion 56a. A polymer insulator being fractured at the intermediate portion 56b and the bottom portion 56c can nevertheless sometimes pass the examination method mentioned above. Since such a fracture can not also be detected from an appearance of the polymer insulator 51 unless the polymer insulator 51 is dismembered, it is necessary to perform a nondestructive inspection method.

SUMMARY OF THE INVENTION

An object of the invention is to eliminate the drawbacks mentioned above and to provide a nondestructive inspection method of a polymer insulator and an apparatus for performing the same in which a securing defect of the polymer insulator can be inspected in a nondestructive manner.

According to the invention, a nondestructive inspection method of measuring a securing defect of a polymer insulator having an FRP core, an outer cover portion arranged around said FRP core, and at least one metal member secured to at least one end of said FRP core, comprises the steps of; measuring an acoustic emission signal generated when said metal member is secured to said FRP core by using compression dies; and determining whether or not said securing defect is generated on the basis of said acoustic emission signal in process, preferably on the basis of a cumulative event count and an oscillation count rate.

Moreover, according to the invention, an apparatus for performing the nondestructive inspection method mentioned above, comprises an acoustic emission sensor arranged to said compression dies for measuring an acoustic emission signal, a control circuit for controlling a movement of said compression dies and a data pick-up interval of said acoustic sensor, a signal processing circuit for processing said acoustic emission signal under the control of said control circuit to obtain a measurement value of said determining parameter, a comparing and determining circuit for determining whether of not said securing defect is generated by comparing an actually measured value of said determining parameter obtained from said signal processing circuit with a reference value of said determining parameter on the basis of a pattern obtained by preliminarily measuring the determining parameter with respect to an actual polymer insulator having the same dimension and the same construction.

In the present invention, a sound generated when the metal member is secured to the FRP core is measured as an acoustic emission signal, and a securing defect is determined on the basis of the measured acoustic emission signal. Therefore, it is possible to detect the securing defect in process.

BRIEF DESCRIPTION OF THE DRAWINGS

FIG. 6 is a graph illustrating a measurement result of an oscillation count rate for the sample in which a defect is simulated; and FIG. 7 is a schematic view depicting one embodiment of a polymer insulator to which the present invention is applied.

DESCRIPTION OF THE PREFERRED EMBODIMENTS

Figure 1:
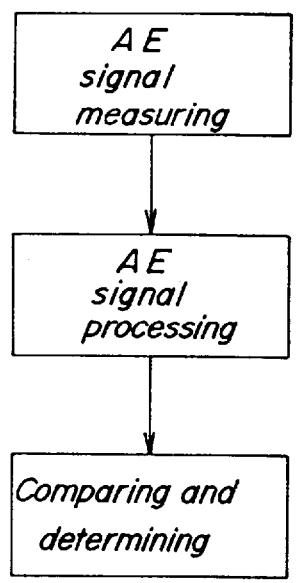
FIG. 1 is a flow chart showing one embodiment of a nondestructive inspection method of a polymer insulator according to the invention.

FIG. 1 is a flow chart showing one embodiment of a nondestructive inspection method of a polymer insulator according to the invention. At first, an acoustic emission (hereinafter referred as AE) signal is measured when a metal member is secured to an FRP core by using compression dies. Then, the thus measured AE signal is processed to obtain preferably a cumulative event count or an oscillation count rate. Finally, a measurement value of an actually measured cumulative event count or an actually measured oscillation count rate is compared with a reference value on the basis of a pattern obtained by preliminarily measuring the cumulative event count or the oscillation count rate with respect to an actual polymer insulator preferably having the same dimension and the same construction as those of the polymer insulator to be measured.

In this embodiment, it is preferred to use the cumulative event count or the oscillation count rate as the determining parameter, but it is possible to use other determining parameters obtained from the AE signal if it has a high correlation with a dimension of the defect.

Here, the reason for preferably using the cumulative event count and the oscillation count rate as the determining parameter is that they are effective for detecting the securing defect, which is a measuring target of the present invention, by using the AE signal. That is to say, the securing defect generated at the securing step is roughly classified into an FRP crack in which a micro crack is generated in the FRP core due to a gradual cutting of glass fibers in the FRP core and an FRP fracture in which the FRP core is fractured due to a sudden cutting of a large number of glass fibers in the FRP core. Since an AE wave-form in the case of the FRP crack has a low amplitude and a continuous shape, it is effective to use the cumulative event count indicating a number of generations of acoustic emission signal as the determining parameter for determining its feature. On the other hand, since the AE wave-form in the case of the FRP fracture has a high amplitude and a sudden shape as compared with those of the FRP crack, it is effective to use the oscillation count rate indicating an oscillation number per one event of the acoustic emission signal as the determining parameter for determining its feature.

One embodiment of a polymer insulator to be inspected is the same as the known polymer insulator as shown in FIG. 7. In FIG. 7, the polymer insulator uses a solid FRP core, but it is possible to apply the nondestructive inspection method according to the invention to a polymer hollow insulator which uses a cylindrical FRP core if the metal members are secured to the both end portions of the cylindrical FRP core as mentioned above.

Figure 2:
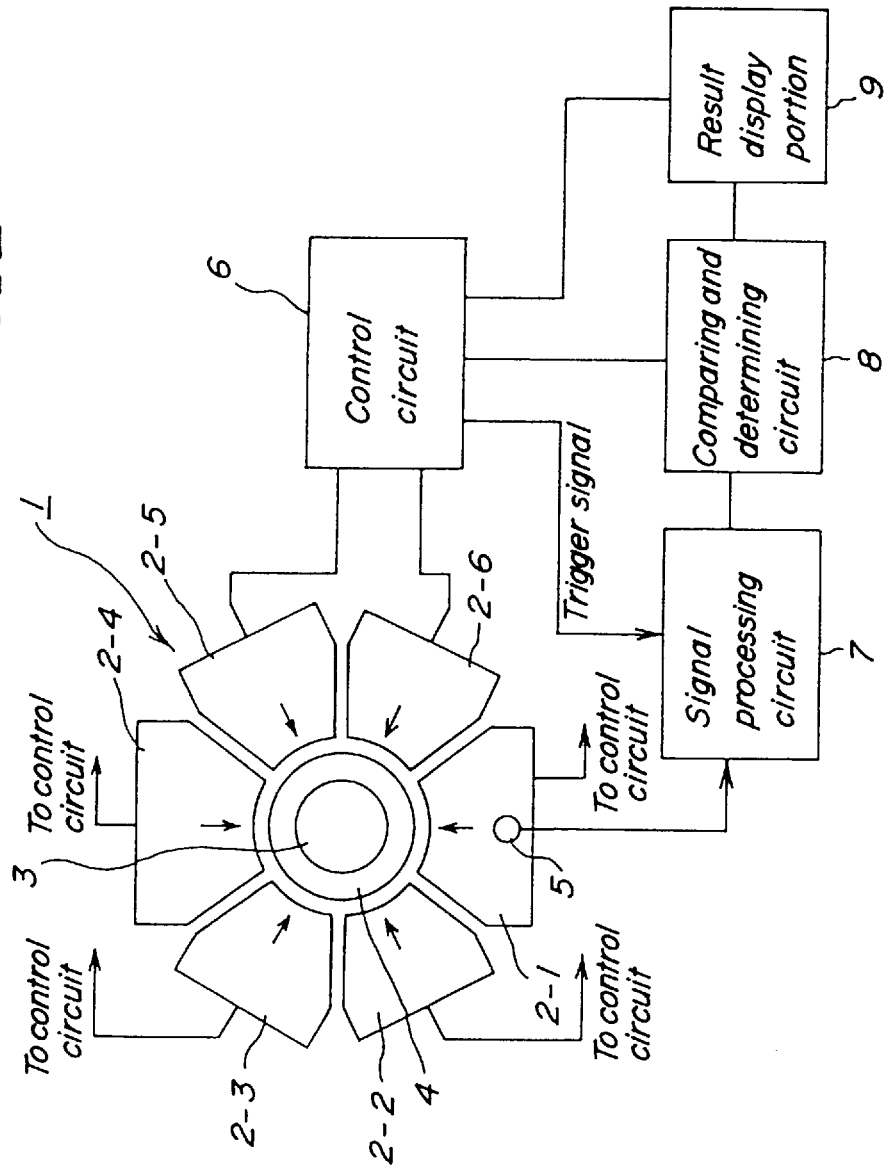
FIG. 2 is a block diagram illustrating one embodiment of an apparatus for performing the nondestructive inspection method according to the invention.

FIG. 2 is a block diagram showing one embodiment of a nondestructive inspection apparatus of the polymer insulator according to the invention. In the embodiment shown in FIG. 2, 1 is a securing apparatus, 2-1 to 2-6 are compression dies, 5 is an AE sensor, 6 is a control circuit, 7 is a signal processing circuit, 8 is a comparing and determining circuit, and 9 is a result display portion. In the securing apparatus 1, the six compression dies 2-1 to 2-6 can apply pressures uniformly to the metal member 4 having a cylindrical shape arranged around the FRP core 3 to secure and fix the metal member 4 to the FRP core 3. The AE sensor 5 for measuring the AE signal generated during the securing step is arranged to the compression die 2-1.

The control circuit 6 is used for controlling movements of the compression dies 2-1 to 2-6 and for transmitting a trigger signal to the signal processing circuit 7. The AE signal measured by the AE sensor 5 is supplied to the signal processing circuit 7. In the signal processing circuit 7, a measuring interval of the AE signal supplied from the AE sensor 5 is controlled in response to the trigger signal supplied from the control circuit 6. That is to say, the AE signal supplied from the AE sensor 5 is picked up only during the interval from a trigger ON signal to a trigger OFF signal. Moreover, the thus picked up AE signal is processed to obtain the cumulative event count. The thus obtained cumulative count event is a number of events when the AE signal pick up operation is finished.

The cumulative event count obtained in the signal processing circuit 7 is transmitted to the comparing and determining circuit 8. In the comparing and determining circuit 8, the thus measured cumulative event count supplied from the signal processing circuit 7 is compared with a reference value of the cumulative event count determined by preliminarily measuring the cumulative event count with respect to an actual polymer insulator. In this comparing step, if the measured cumulative event count is larger than the reference value of the cumulative event count, it is determined as a securing defect. Contrary to this, if the measured cumulative event count is smaller than the reference number of the cumulative event count, it is determined as no securing defect. Finally, the result obtained from the comparing and determining circuit 8 is displayed on the result display portion 9 such as CRT, printer, and so on. In this embodiment mentioned above, the cumulative event count is explained as the determining parameter, but the same operations as those of the embodiment mentioned above can be applied to the nondestructive inspection apparatus using the oscillation count rate as the determining parameter.

In this embodiment, as one example of the nondestructive inspection apparatus, an AE measurement system manufactured by NF circuit design block co., ltd. (product name: MUSIC) can be preferably used.

Figure 3:
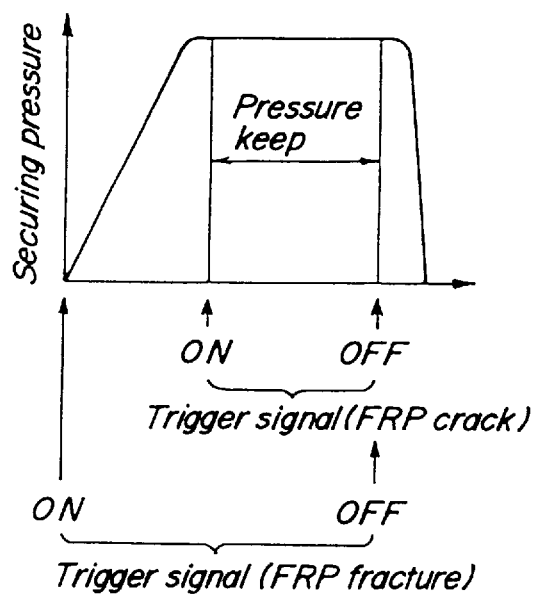
FIG. 3 is a graph depicting one preferable embodiment of a variation of a securing pressure during a securing step according to the invention.

FIG. 3 is a graph showing one example of a variation of securing pressure in the securing step according to a preferable embodiment of the invention. In the example shown in FIG. 3, securing pressures of the compression dies 2-1 to 2-6 are gradually increased and then kept constantly for 8 seconds. Then, if the trigger ON signal is supplied from the control circuit 6 to the signal processing circuit 7, the pick up operation of the AE signal from the AE sensor 5 is started. If the trigger OFF signal is supplied from the control circuit 6 to the signal processing circuit 7, the pick up operation of the AE signal from the AE sensor 5 is terminated.

In FIG. 3, in the case of using the cumulative event count as the determining parameter, the trigger ON signal is generated at a start of a pressure keep interval, and the trigger OFF signal is generated at an end of the pressure keep interval. Moreover, the pressure keep interval from the trigger ON signal to the trigger OFF signal is set to 8 seconds, and the AE signal is picked up only for the pressure keep interval of 8 seconds. In this manner, the reason for picking up the AE signal only for the pressure keep interval in the case of using the cumulated event count as the determining parameter is as follows. That is to say, a noise due to a mechanical movement of the compression dies or the like under a pressure increase state in the securing step is larger than a sound of crack generations in the FRP core, and also such a noise is small under a pressure keep state. Therefore, if the AE signal is picked up only for the pressure keep interval, it is possible to obtain the AE signal having small noise. As a result, it is possible to perform the nondestructive inspection method in a highly precise manner.

Further, in FIG. 3, in the case of using the oscillation count rate as the determining parameter, the trigger ON signal is generated at a start of a pressure apply operation, and the trigger OFF signal is generated at an end of the pressure keep interval. This is because a fracture of the FRP core is sometimes generated under the pressure increase state from the start of the pressure apply operation. Moreover, since a number of oscillation of the AE signal due to this fracture is larger than that of the noise mentioned above, it is possible to determine the fracture of the FRP core without being affected by the noise mentioned above if classifying it by using the oscillation count rate as the determining parameter.

Figure 4A:
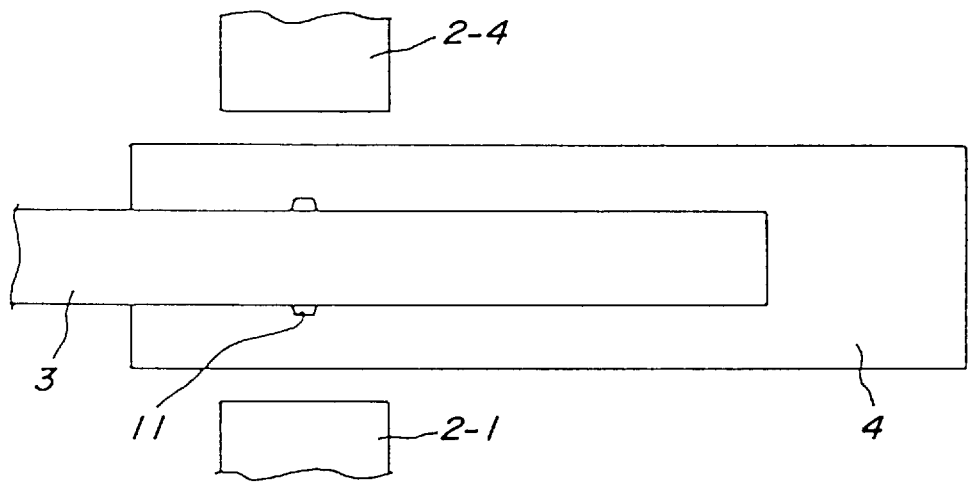
FIGS. 4a and 4b are schematic view for explaining a sample in which a defect is simulated according to the invention.
Figure 4B:
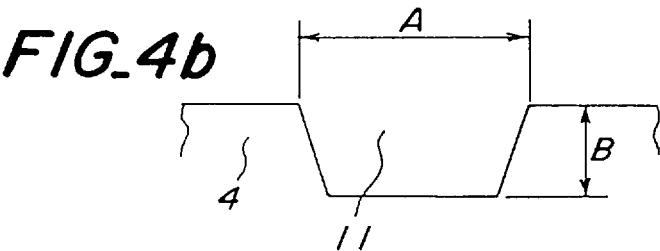

Then, in order to examine a relation between an area of the FRP crack and the cumulative event count, a sample in which a defect is simulated and a result of measuring the cumulative event count with respect to the sample mentioned above will be explained. At first, as the sample in which the defect is simulated, an FRP core 3 made of one-way deforming FRP having a diameter of 16 mm was inserted into a hollow portion of a metal member 4 made of a carbon steel for a construction member having an inner diameter of 16 mm and an outer diameter of 28 mm, as shown in FIG. 4a. in this case, a defect 11 was formed in an inner surf ace of the metal member at portions opposed to the compression dies 2-1 and 2-4 each having a width of a connection surface of 20 mm. Moreover, as shown in FIG. 4b, samples having five levels as shown in Table 1 were prepared by controlling width A and a depth B of the defect 11.

TABLE 1

| Simulated sample level | 1 | 2 | 3 | 4 | 5 |
|---|---|---|---|---|---|
| A (mm) | 0.2 | 0.4 | 0.6 | 0.8 | 1.0 |
| B (mm) | 0.01 | 0.02 | 0.03 | 0.04 | 0.05 |

Then, the securing operation was performed actually in the manner shown in FIG. 3 by using the compression dies 2-1 to 2-6 of the nondestructive inspection apparatus having the construction shown in FIG. 2, and the cumulative event count were measured only for the pressure keep interval of 8 seconds. The result shown in FIG. 5 was obtained from overall 50 samples. From the result shown in FIG. 5, it is understood that an FRP crack area indicating an overall area of cracks generated on a surface of the FRP core 3 is highly correlated with the cumulative event count and thus it is possible to measure the FRP crack area generated in the FRP core 3 by measuring the cumulative event count. As a result, it is understood that it is possible to perform the nondestructive inspection for the polymer insulator by using a reference value of the cumulative event count determined on the basis of a pattern obtained by preliminarily measuring the cumulative event count with respect to an actual polymer insulator.

Figure 5:
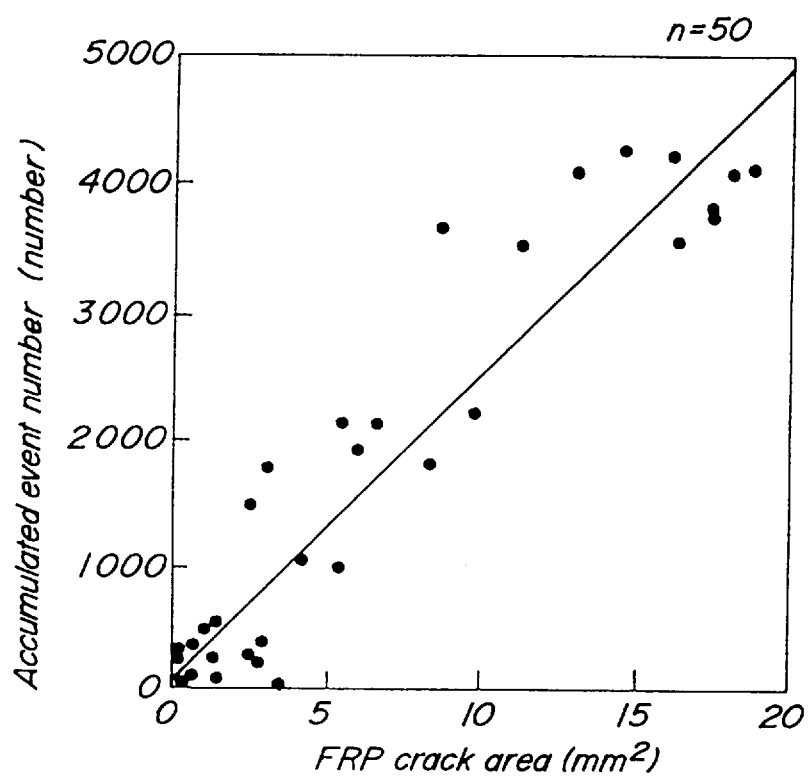
FIG. 5 is a graph showing a relation between a cumulative event count and an FRP crack area of a sample in which a defect is simulated.

Therefore, if the relation as shown in FIG. 5 is preliminarily formed from the actual polymer insulator and the actual nondestructive measurement is performed under the condition such that the cumulative event count of 1000 is assumed as the reference value, it is possible to determine whether or not the securing defect is generated. That is to say, by using the FRP crack area of 3 $mm^2$ as a threshold value, if the cumulative event count is smaller than the threshold value it is examined that the securing defect is not generated due to the FRP crack, and if the cumulative event count is larger than the threshold value it is examined that the securing defect is generated due to the FRP crack. In this case, if use is made of the cumulative event count mentioned above as the reference value, it is confirmed that the nondestructive inspection of the polymer insulator is successively performed.

Then, in order to examine a relation between the FRP fracture and the oscillation count rate, a result of measuring the oscillation count rate as the determining parameter with respect to the sample in which the defect is simulated will be explained. At first, the FRP core 3 and the metal member 4 having the same dimension as that of the embodiment mentioned above were prepared. In ten samples among them, a larger defect as that of the embodiment mentioned above was formed circumferentially in an inner surface of the metal member 4. Then, the securing operation was performed actually in the manner shown in FIG. 3 by using the compression dies 2-1 to 2-6 of the nondestructive inspection apparatus having the construction shown in FIG. 2, and the oscillation count rate was measured from a start of the pressure apply operation to an end of the pressure keep interval. In this case, a larger pressure than that during the pressure keep interval shown in FIG. 3 was applied to a part of the samples. After that, the FRP core 3 and the metal member 4 were cut out to determine whether or not the FRP fracture was generated. The results for overall 391 samples were shown in FIG. 6.

From the result shown in FIG. 6, since both of the samples fractured due to the defect on an inner surface of the metal member and fractured due to an excessive pressure show a higher oscillation count rate than that of the samples having no FRP fracture, it is understood that it is possible to determine whether or not the FRP fracture is generated by measuring the oscillation count rate. As a result, it is understood that it is possible to perform the nondestructive inspection for the polymer insulator by using a reference value of the oscillation count rate determined on the basis of a pattern obtained by preliminarily measuring the oscillation count rate with respect to an actual polymer insulator. Therefore, if the relation as shown in FIG. 6 is preliminarily formed from the actual polymer insulator and the actual nondestructive inspection is performed under the condition such that the oscillation count rate of $4.5 \times 10^5$ number/event is assumed as the reference value, it is possible to determine whether or not the FRP fracture is generated. In this case, if use is made of the oscillation count rate mentioned above as the reference value, it is confirmed that the nondestructive inspection of the polymer insulator is successively performed.

As can be understood from the above explanations, according to the invention, since a sound generated when the metal member is secured to the FRP core is measured as an acoustic emission signal, and a securing defect is determined on the basis of the measured acoustic emission signal, it is possible to detect the securing defect in process.

What is claimed is:

1. A nondestructive inspection method of inspecting a securing defect of a polymer insulator having an FRP core, an outer cover portion arranged around said FRP core, and at least one metal member secured to at least one end of said FRP core, comprising the steps of;

measuring an acoustic emission signal generated when said metal member is secured to said FRP core by using compression dies; and determining whether or not said securing defect is generated on the basis of said acoustic emission signal in process.

2. The nondestructive inspection method according to claim 1, wherein said securing by using the compression dies is performed by keeping a pressure applied to said metal member constant for several seconds to measure said acoustic emission signal only during said pressure keeping interval.

3. The nondestructive inspection method according to claim 1, wherein said securing defect determining is performed by using a cumulative event count of said acoustic emission signal as a determining parameter in such a manner that an actually measured cumulative event count is compared with a reference value of the cumulative event count determined on the basis of a pattern obtained by preliminarily measuring the cumulative event count with respect to an actual polymer insulator.

4. The nondestructive inspection method according to claim 1, wherein said securing defect determining is performed by using an oscillation count rate of said acoustic emission signal as a determining parameter in such a manner that an actually measured oscillation count rate of said acoustic emission signal is compared with a reference value of the oscillation count rate determined on the basis of a pattern obtained by preliminarily measuring the oscillation count rate with respect to an actual polymer insulator.

5. An apparatus for performing the nondestructive inspection method set forth in claim 1, comprising an acoustic emission sensor arranged with said compression dies for measuring an acoustic emission signal, a control circuit for controlling a movement of said compression dies and a data pick-up interval of said acoustic sensor, a signal processing circuit for processing said acoustic emission signal under the control of said control circuit to obtain a measurement value of said determining parameter, a comparing and determining circuit for determining whether of not said securing defect is generated by comparing an actually measured value of said determining parameter obtained from said signal processing circuit with a reference value of said determining parameter on the basis of a pattern obtained by preliminarily measuring the determining parameter with respect to an actual polymer insulator.

6. The apparatus according to claim 5, wherein said determining parameter is a cumulative event count of said acoustic emission signal.

7. The apparatus according to claim 5, wherein said determining parameter is an oscillation count rate of said acoustic emission signal.

* * * * *